(12) United States Patent
Velaparthi et al.

(10) Patent No.: US 8,212,031 B2
(45) Date of Patent: Jul. 3, 2012

(54) PYRROLOTRIAZINE KINASE INHIBITORS

(75) Inventors: Upender Velaparthi, Cheshire, CT (US); Dolatrai M. Vyas, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 61 days.

(21) Appl. No.: 12/920,511

(22) PCT Filed: Mar. 4, 2009

(86) PCT No.: PCT/US2009/035975
§ 371 (c)(1), (2), (4) Date: Sep. 1, 2010

(87) PCT Pub. No.: WO2009/111531
PCT Pub. Date: Sep. 11, 2009

(65) Prior Publication Data
US 2011/0003821 A1    Jan. 6, 2011

Related U.S. Application Data

(60) Provisional application No. 61/034,171, filed on Mar. 6, 2008.

(51) Int. Cl.
*C07D 253/08* (2006.01)
(52) U.S. Cl. ........................ 544/183; 514/243
(58) Field of Classification Search ............... 514/243; 544/183
See application file for complete search history.

(56) References Cited

U.S. PATENT DOCUMENTS

| 7,531,539 B2 | 5/2009 | Fink et al. | |
|---|---|---|---|
| 7,534,792 B2 | 5/2009 | Wittman et al. | |
| 2007/0270412 A1* | 11/2007 | Bell et al. | 514/218 |
| 2011/0294816 A1* | 12/2011 | Purandare et al. | 514/243 |

FOREIGN PATENT DOCUMENTS

| WO | WO 2008/005956 | 1/2008 |
|---|---|---|
| WO | WO 2008/021924 | 2/2008 |
| WO | WO 2008/131050 | 10/2008 |

* cited by examiner

*Primary Examiner* — James O Wilson
*Assistant Examiner* — Alexander R Pagano
(74) *Attorney, Agent, or Firm* — Elliott Korsen

(57) ABSTRACT

The invention provides compounds of formula I

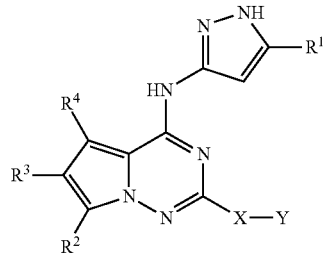

and pharmaceutically acceptable salts thereof.
The formula I compounds inhibit protein kinase activity thereby making them useful as anticancer agents.

9 Claims, No Drawings

PYRROLOTRIAZINE KINASE INHIBITORS

FIELD OF THE INVENTION

The invention relates to novel pyrrolotriazine compounds that are useful as inhibitors of tyrosine kinases. This invention also relates to pharmaceutical compositions containing the compounds and methods of using the compounds for the treatment of proliferative and other diseases, in particular, certain types of cancer.

BACKGROUND

The invention relates to compounds which inhibit tyrosine kinase enzymes, compositions which contain tyrosine kinase inhibiting compounds and methods of using inhibitors of tyrosine kinase enzymes to treat diseases which are characterized by an overexpression or upregulation of tyrosine kinase activity such as cancer, diabetes, restenosis, arteriosclerosis, psoriasis, Alzheimer's disease, angiogenic diseases and immunologic disorders (Powis, G.; Workman P. Signaling Targets For The Development of Cancer Drugs. *Anti-Cancer Drug Design* (1994), 9: 263-277; Merenmies, J.; Parada, L. F.; Henkemeyer, M. Receptor Tyrosine Kinase Signaling in Vascular Development. *Cell Growth Differ* (1997) 8: 3-10; Shawver, L. K.; Lipsosn, K. E.; Fong, T. A. T.; McMahon, G.; Plowman, G. D.; Strawn, L. M. Receptor Tyrosine Kinases As Targets For Inhibition of Angiogenesis. *Drug Discovery Today* (1997) 2: 50-63; all herein incorporated by reference).

Tyrosine kinases play a critical role in signal transduction for several cellular functions including cell proliferation, carcinogenesis, apoptosis, and cell differentiation. Inhibitors of these enzymes are useful for the treatment or prevention of proliferative diseases which are dependent on these enzymes. Strong epidemiologic evidence suggests that the overexpression or activation of receptor protein tyrosine kinases leading to constitutive mitogenic signaling is an important factor in a growing number of human malignancies. Tyrosine kinases that have been implicated in these processes include Abl, CDK's, EGF, EMT, FGF, FAK, Flk-1/KDR, Flt-3, GSK-3, GSKbeta-3, HER-2, IGF-1R, IR, Jak2, LCK, MET, PDGF, Src, Tie-2, TrkA, TrkB and VEGF. Hence, there is an ongoing need to investigate novel compounds that can be used to regulate or inhibit tyrosine kinase enzymes.

It is also desirable and preferable to find compounds with advantageous and improved characteristics in one or more of the following categories, which are given as examples and are not intended to be limiting: (a) pharmacokinetic properties, including oral bioavailability; (b) pharmaceutical properties; (c) dosage requirements; (d) factors which decrease blood concentration peak-to-trough characteristics; (e) factors that increase the concentration of active drug at the receptor; (f) factors that decrease the liability for clinical drug-drug interactions; (g) factors that decrease the potential for adverse side-effects; and (h) factors that improve manufacturing costs or feasibility.

SUMMARY OF THE INVENTION

The invention provides compounds of Formula I, including stereoisomers, tautomers and pharmaceutically acceptable salts thereof, which are useful as inhibitors of tyrosine kinase enzymes.

The invention also provides pharmaceutical compositions comprising a pharmaceutically acceptable carrier and one or more of the compounds of the present invention or a stereoisomer, tautomer or pharmaceutically acceptable salt thereof.

The invention also provides a method for treating a condition associated with one or more tyrosine kinase inhibitors comprising administering to a patient in need of such treatment, a therapeutically effective amount of a compound of formula I or a stereoisomer, tautomer or pharmaceutically acceptable salt thereof, and optionally one or more other anticancer agent or treatment.

The invention also provides methods for treating cancer using the compounds of the invention or a stereoisomer, tautomer or pharmaceutically acceptable salt thereof.

The invention also provides the compounds of the present invention or a stereoisomer, tautomer or pharmaceutically acceptable salt thereof, for use in therapy.

The present invention also provides the use of the compounds of the present invention or a stereoisomer, tautomer or pharmaceutically acceptable salt thereof, for the manufacture of a medicament for the treatment of a proliferative disease such as cancer.

These and other features of the invention will be set forth in the expanded form as the disclosure continues.

DETAILED DESCRIPTION OF THE INVENTION

The invention provides for compounds of formula I, pharmaceutical compositions employing such compounds and for methods of using such compounds.

In one aspect of the invention, there are disclosed compounds of formula I

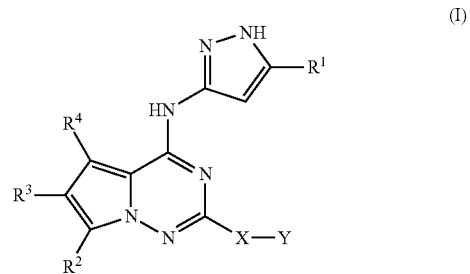

wherein:

X is a heterocyclyl group containing 2 or more heteroatoms;

Y is $COR^5$ or $CONHR^5$;

$R^1$ is hydrogen, alkyl, substituted alkyl, amide, substituted amide, cycloalkyl or substituted cycloalkyl;

$R^2$, $R^3$ and $R^4$ are independently hydrogen, alkyl, substituted alkyl, hydroxy, alkoxy, substituted alkoxy, halogen, amino, substituted amino, aminoalkyl, substituted aminoalkyl, alkylamino, substituted alkylamino, amide, substituted amide, carbamate, ureido or —CN;

$R^5$ is heteroaryl or substituted heteroaryl, or a pharmaceutically acceptable salt, tautomer or stereoisomer thereof.

In a second embodiment, the invention comprises a compound of formula I

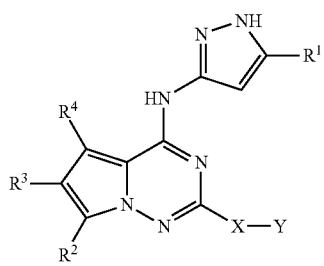

(I)

wherein
X is pyrazolidine or piperazine;
$R^1$ is cycloalkyl or substituted cycloalkyl;
$R^5$ is thiazole, pyrazine or substituted pyrazine, pyridine or substituted pyridine,
or a pharmaceutically acceptable salt or stereoisomer thereof.

In a third embodiment, the invention comprises a compound of formula I wherein:
$R^2$, $R^3$ and $R^4$ are independently hydrogen or $C_1$-$C_4$ alkyl.
Compounds of the invention include the following
2-(4-(3-Cyclopropyl-1H-pyrazol-5-ylamino)pyrrolo[1,2-f][1,2,4]triazin-2-yl)-N-(6-fluoropyridin-3-yl)pyrazolidine-1-carboxamide,
2-(4-(3-cyclopropyl-1H-pyrazol-5-ylamino)pyrrolo[1,2-f][1,2,4]triazin-2-yl)-N-(6-fluoropyridin-3-yl)piperazine-1-carboxamide,
2-(4-(3-Cyclopropyl-1H-pyrazol-5-ylamino)pyrrolo[1,2-f][1,2,4]triazin-2-yl)-N-(thiazol-2-yl)piperazine-1-carboxamide,
(2-(4-(3-cyclopropyl-1H-pyrazol-5-ylamino)pyrrolo[1,2-f][1,2,4]triazin-2-yl)piperazin-1-yl)(thiazol-2-yl)methanone,
(2-(4-(3-Cyclopropyl-1H-pyrazol-5-ylamino)pyrrolo[1,2-f][1,2,4]triazin-2-yl)piperazin-1-yl)(6-fluoropyridin-3-yl)methanone, and
(2-(4-(3-Cyclopropyl-1H-pyrazol-5-ylamino)pyrrolo[1,2-f][1,2,4]triazin-2-yl)piperazin-1-yl)(pyrazin-2-yl)methanone,
or a pharmaceutically acceptable salt thereof.

In another embodiment the present invention provides a pharmaceutical composition comprising a pharmaceutically acceptable carrier and one or more of the compounds of the present invention or a stereoisomer, tautomer or pharmaceutically acceptable salt thereof.

In another embodiment the present invention provides a pharmaceutical composition comprising a pharmaceutically acceptable carrier and a therapeutically effective amount of one or more of the compounds of the present invention or a stereoisomer, tautomer or pharmaceutically acceptable salt thereof.

In another embodiment the present invention provides a method for treating protein kinase related disorders comprising: administering to a patient in need of such treatment a therapeutically effective amount of one or more of the compounds of the present invention or a stereoisomer, tautomer or pharmaceutically acceptable salt thereof.

In another embodiment the present invention provides a method for treating tyrosine kinase related disorders comprising: administering to a patient in need of such treatment a therapeutically effective amount of one or more of the compounds of the present invention or a stereoisomer, tautomer or pharmaceutically acceptable salt thereof.

In another embodiment, the protein kinase related disorder is selected from the group consisting of cancer of the prostate, pancreatic ductal adreno-carcinoma, breast, colon, lung, ovary, pancreas, thyroid, neuroblastoma, glioblastoma, medulloblastoma, melanoma, multiple myeloma or acute myelogenous leukemia (AML).

In another embodiment, the present invention provides a method of treating a patient in need of protein kinase related disorder treatment, comprising: administering a compound of the present invention or a stereoisomer, tautomer or pharmaceutically acceptable salt thereof in an amount effective to treat a protein kinase related disorder.

In another embodiment, the present invention provides a pharmaceutical composition further comprising one or more additional anticancer agent or treatment, such as radiation therapy.

In another embodiment, the present invention provides a compound of the present invention for use in therapy.

In another embodiment, the present invention provides a compound of the present invention for use in therapy for treating a protein kinase related disorder.

In another embodiment, the present invention provides a compound of the present invention for use in therapy for treating a tyrosine kinase related disorder.

In another embodiment, the present invention also provides the use of a compound of the present invention for the manufacture of a medicament for the treatment of a protein kinase related disorder.

In another embodiment, the present invention also provides the use of a compound of the present invention for the manufacture of a medicament for the treatment of a tyrosine kinase related disorder.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment of a protein kinase related disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

The following are definitions of terms that may be used in the specification. The initial definition provided for a group or term herein applies to that group or term throughout the specification individually or as part of another group, unless otherwise indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N).

When any variable (e.g., $R^3$) occurs more than one time in any constituent or formula for a compound, its definition at each occurrence is independent of its definition at every other occurrence. Thus, for example, if a group is shown to be substituted with 0-2 $R^3$, then said group may optionally be substituted with up to two $R^3$ groups and $R^3$ at each occurrence is selected independently from the definition of $R^3$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

In cases wherein there are nitrogen atoms (e.g., amines) on compounds of the invention, these can be converted to N-oxides by treatment with an oxidizing agent (e.g., MCPBA and/or hydrogen peroxides) to afford other compounds of this invention. Thus, all shown and claimed nitrogen atoms are considered to cover both the shown nitrogen and its N-oxide (N→O) derivative.

The term "alkyl" or "aklylene" refers to both branched and straight-chain saturated aliphatic hydrocarbon groups of 1 to 20 carbon atoms, preferably 1 to 7 carbon atoms. The expression "lower alkyl" refers to unsubstituted alkyl groups of 1 to 4 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or arylalkyl.

The term "cycloalkyl" refers to an optionally substituted, saturated cyclic hydrocarbon ring systems, preferably containing 1 to 3 rings and 3 to 7 carbons per ring which may be further fused with an unsaturated $C_3$-$C_7$ carbocyclic ring. Exemplary groups include cyclopropyl, cyclobutyl, cyclopentyl, cyclohexyl, cycloheptyl, cycloctyl, cyclodecyl, cyclododecyl, and adamantyl. Exemplary substituents include one or more alkyl groups as described above, or one or more groups described above as alkyl substituents.

The term "alkoxy" or "alkyloxy" refers to an alkyl group as defined above with the indicated number of carbon atoms attached through an oxygen bridge. For example, "$C_{1-6}$ alkoxy" (or alkyloxy), is intended to include $C_1$, $C_2$, $C_3$, $C_4$, $C_5$, and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" or "thioalkoxy" represents an alkyl group as defined above with the indicated number of carbon atoms attached through a sulphur bridge; for example methyl-S—, ethyl-S—, and the like. Exemplary substituents include one or more alkyl groups as described above, or one or more groups described above as alkyl substituents.

The term "halogen" or "halo" refers to fluorine, chlorine, bromine and iodine.

The term "haloalkyl" is intended to include both branched and straight-chain saturated aliphatic hydrocarbon groups having the specified number of carbon atoms, substituted with 1 or more halogen. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" which is intended to include both branched and straight-chain saturated aliphatic hydrocarbon groups having the specified number of carbon atoms, substituted with 1 or more fluorine atoms.

The term "haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

The term "carbocyclic ring" or "carbocyclyl" refers to stable 3, 4, 5, 6, 7, or 8-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred carbocycles, unless otherwise specified, are cyclopropyl, cyclobutyl, cyclopentyl, cyclohexyl, phenyl, and indanyl. When the term "carbocycle" is used, it is intended to include "aryl".

As used herein, the term "bicyclic carbocycle" or "bicyclic carbocyclic group" refers to a stable 9 or 10-membered carbocyclic ring system which contains two fused rings and consists of carbon atoms. Of the two fused rings, one ring is a benzo ring fused to a second ring; and the second ring is a 5 or 6 membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

The term "optionally substituted" as it refers to "carbocyclic ring" or "carbocyclyl" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The terms "aryloxy", "arylamino", "arylalkylamino", "arylthio", "arylalkanoylamino", "arylsulfonyl", "arylalkoxy", "arylsulfinyl", "arylheteroaryl", "arylalkylthio", "arylcarbonyl", "arylalkenyl", or "arylalkylsulfonyl" refer to an aryl or substituted aryl bonded to an oxygen; an amino; an alkylamino; a thio; an alkanoylamino; a sulfonyl; an alkoxy; a sulfinyl; a heteroaryl or substituted heteroaryl; an alkylthio; a carbonyl; an alkenyl; or an alkylsulfonyl, respectively.

The term "arylsulfonylaminocarbonyl" refers to an arylsulfonyl bonded to an aminocarbonyl.

The terms "aryloxyalkyl", "aryloxycarbonyl" or "aryloxyaryl" refer to an aryloxy bonded to an alkyl or substituted alkyl; a carbonyl; or an aryl or substituted aryl, respectively.

The term "arylalkyl" refers to an alkyl or substituted alkyl in which at least one of the hydrogen atoms bonded to at least one of the carbon atoms is replaced with an aryl or substituted aryl. Typical arylalkyls include, but are not limited to, for example, benzyl, 2-phenylethan-1-yl, 2-phenylethen-1-yl, naphthylmethyl, 2-naphthylethan-1-yl, 2-naphthylethen-1-yl, naphthobenzyl, and 2-naphthophenylethan-1-yl.

The term "arylalkyloxy" refers to an arylalkyl bonded through an oxygen linkage (—O-arylalkyl).

The term "substituted aryl" refers to an aryl group substituted by, for example, one to four substituents such as alkyl, substituted alkyl, alkenyl, substituted alkenyl, alkynyl, substituted alkynyl, aryl, substituted aryl, arylalkyl, halo, trifluoromethoxy, trifluoromethyl, hydroxy, alkoxy, alkanoyl, alkanoyloxy, aryloxy, arylalkyloxy, amino, alkylamino, arylamino, arylalkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or arylalkyl.

The term "heteroaryl" refers to an optionally substituted, stable monocyclic and polycyclic aromatic hydrocarbons that include at least one heteroatom ring member such as sulfur, oxygen, or nitrogen. Preferred heteroaryl groups are stable 5, 6, or 7-membered monocyclic or 7, 8, 9, or 10-membered bicyclic heterocyclic aromatic rings which consists of carbon atoms and 1, 2, 3, or 4 heteroatoms independently selected from the group consisting of N, NH, O and S. It is to be noted that total number of S and O atoms in the aromatic heterocycle is not more than 1. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, oxadiazolyl, benzofuryl, benzothienyl, benzthiazolyl, isoxazolyl, pyrazolyl, triazolyl, tetrazolyl indazolyl, 1,2,4-thiadiazolyl, isothiazolyl, benzothienyl, purinyl, carbazolyl, benzimidazolyl, 2,3-dihydrobenzofuranyl, 2,3-dihydrobenzothienyl, 2,3-dihydrobenzothienyl-S-oxide, 2,3-dihydrobenzothienyl-S-dioxide, benzoxazolin-2-on-yl, indolinyl, benzodioxolanyl, benzodioxane, and the like.

Heteroaryl groups can be substituted or unsubstituted.

Exemplary substituents include one or more alkyl or arylalkyl groups as described above or one or more groups described above as alkyl substituents.

The terms "heterocycle", "heterocyclic" and "heterocyclyl" refer to an optionally substituted, saturated, partially unsaturated or fully unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized to —NO—, —SO—, or —SO$_2$— and the nitrogen heteroatoms may also optionally be quaternized. The heterocyclic group may be attached at any heteroatom or carbon atom. When the term "heterocycle" is used, it is intended to include heteroaryl.

Examples of heterocycles include, but are not limited to, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, 1,3-benzodioxolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, pyrrolotriazinyl, quinazolinyl, tetrahydroquinolinyl, thienofuryl, thienopyridyl, thienothienyl, and the like.

Exemplary substituents include one or more alkyl or arylalkyl groups as described above or one or more groups described above as alkyl substituents.

Also included are smaller heterocyclyls, such as, epoxides and aziridines.

The term "heteroatoms" shall include oxygen, sulfur and nitrogen.

The term "alkylsulfone" refers to $—R^kS(=O)_2R^k$, wherein $R^k$ is an alkyl or substituted alkyl.

The term "oxo" refers to the divalent radical $=O$.

The term "carbamate" refers to the group $—OC(=O)NH_2$.

The term "amide" refers to the group $—C(=O)NH_2$.

The term "sulfonamide" refers to the group $—SO_2NH_2$.

The terms "substituted amide", "substituted sulfonamide", or "substituted carbamate" refer to an amide, sulfonamide, or carbamate, respectively, having at least one hydrogen replaced with a group chosen from alkyl, substituted alkyl, alkenyl, substituted alkenyl, cycloalkyl, and substituted cycloalkyl.

A substituted amide, for example, refers to the group $—C(=O)NR^mR^n$ wherein $R^m$ and $R^n$ are independently selected from H, alkyl, substituted alkyl, alkenyl, substituted alkenyl, cycloalkyl, and substituted cycloalkyl, provided at least one of $R^m$ or $R^n$ is a substituted moiety.

A substituted sulfonamide, for example, refers to the group $—SO_2NR^oR^p$ wherein $R^o$ and $R^p$ are independently selected from alkyl, substituted alkyl, alkenyl, substituted alkenyl, cycloalkyl, and substituted cycloalkyl, provided at least one of $R^o$ or $R^p$ is a substituted moiety.

A substituted carbamate, for example, refers to the group $—OC(=O)NR^qR^r$ wherein $R^q$ and $R^r$ are independently selected from alkyl, substituted alkyl, alkenyl, substituted alkenyl, cycloalkyl, and substituted cycloalkyl, provided at least one of $R^q$ or $R^r$ is a substituted moiety.

The term "ureido" refers to the group $—NHC(=O)NH_2$.

The term "cyano" refers to the group $—CN$.

The terms "cycloalkylalkyl" or "cycloalkylalkoxy" refer to a cycloalkyl or substituted cycloalkyl bonded to an alkyl or substituted alkyl; or an alkoxy, respectively.

The term "nitro" refers to the group $—N(O)_2$.

The term "thio" refers to the group $—SH$.

The term "alkylthio" refers to the group $—SR^s$ where $R^s$ is an alkyl, substituted alkyl, cycloalkyl, or substituted cycloalkyl.

The term "thioalkyl" refers to the group $—R^tS$ where $R^t$ is an alkyl, substituted alkyl, cycloalkyl, or substituted cycloalkyl.

The term "alkylsulfonyl" refers to the group $—S(=O)_2R^u$ where $R^u$ is an alkyl, substituted alkyl, cycloalkyl, or substituted cycloalkyl.

The term "alkylsulfinyl" refers to the group $—S(=O)R^v$ where $R^v$ is an alkyl, substituted alkyl, cycloalkyl, or substituted cycloalkyl.

The term "carboxy" refers to the group $—C(=O)OH$.

The terms "carboxyalkoxy" or "alkoxycarbonylalkoxy" refer to a carboxy, or an alkoxycarbonyl, respectively, bonded to an alkoxy.

The term "alkoxycarbonyl" refers to the group $—C(=O)OR^w$ where $R^w$ is an alkyl, substituted alkyl, cycloalkyl, substituted cycloalkyl, aryl, substituted aryl, heteroaryl, or substituted heteroaryl.

The term "arylalkoxycarbonyl" refers to an aryl or substituted aryl bonded to an alkoxycarbonyl.

The terms "alkylcarbonyloxy" or "arylcarbonyloxy" refer to the group $—OC(=O)R^x$, where $R^x$ is an alkyl or substituted alkyl, or an aryl or substituted aryl, respectviely.

The term "carbamoyl" refers to the groups $—OC(=O)NH_2$, $—OC(=O)NHR^x$, and/or $—OC(=O)NR^yR^z$, wherein $R^y$ and $R^z$ are independently selected from alkyl and substituted alkyl.

The group $—NR^6(C=O)R^9$ refers to a group where $R^6$ is selected from hydrogen, lower alkyl and substituted lower alkyl, and $R^9$ is selected from hydrogen, alkyl, substituted alkyl, alkoxy, aminoalkyl, substituted aminoalkyl, alkylamino, substituted alkylamino, aryl and substituted aryl.

The term "carbonyl" refers to a $C(=O)$.

The terms "alkylcarbonyl", "aminocarbonyl", "alkylaminocarbonyl" "aminoalkylcarbonyl", or "arylaminocarbonyl" refer to an alkyl or substituted alkyl; an amino; an alkylamino or substituted alkylamino; an aminoalkyl or substituted aminoalkyl; or an arylamino, respectively, bonded to a carbonyl.

The terms "aminocarbonylaryl" or "aminocarbonylalkyl" refer to an aminocarbonyl bonded to an aryl or substituted aryl; or an alkyl or substituted alkyl, respectively.

The term "sulfonyl" refers to the group $S(=O)_2$.

The term "sulfinyl" refers to an $S(=O)$.

The term "carboxyalkyl" refers to an alkyl or substituted alkyl bonded to a carboxy.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed according to methods known to those skilled in the art.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures. It very particularly embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

The present invention is also intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds of the formula I may also have prodrug forms. Since prodrugs are known to enhance numerous desirable qualities of pharmaceuticals (e.g., solubility, bioavailability, manufacturing, etc.) the compounds of the invention may be delivered in prodrug form. Thus, the invention is intended to cover prodrugs of the claimed compounds, methods of delivering the same and compositions containing the same. "Prodrugs" are intended to include any covalently bonded carriers that release an active parent drug of the invention in vivo when such prodrug is administered to a mammalian subject. Prodrugs of the invention are prepared by modifying functional groups present in the compound in such a way that the modifications are cleaved, either in routine manipulation or in vivo, to the parent compound. Prodrugs include compounds of the invention wherein a hydroxy, amino, or sulfhydryl group is bonded to any group that, when the prodrug of the invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the invention.

Various forms of prodrugs are well known in the art. For examples of such prodrug derivatives, see:
- a) *Design of Prodrugs*, edited by H. Bundgaard, (Elsevier, 1985), and *Methods in Enzymology*, Vol. 42, at pp. 309-396, edited by K. Widder, et. al. (Academic Press, 1985);
- b) *A Textbook of Drug Design and Development*, edited by Krosgaard-Larsen and H. Bundgaard, Chapter 5, "Design and Application of Prodrugs," by H. Bundgaard, at pp. 113-191 (1991);
- c) H. Bundgaard, *Advanced Drug Delivery Reviews*, Vol. 8, p. 1-38 (1992);
- d) H. Bundgaard, et al., *Journal of Pharmaceutical Sciences*, Vol. 77, p. 285 (1988); and
- e) N. Kakeya, et. al., *Chem Phar Bull.*, Vol. 32, p. 692 (1984).

Compounds containing a carboxy group can form physiologically hydrolyzable esters which serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Preparation of prodrugs is well known in the art and described in, for example, *Medicinal Chemistry: Principles and Practice*, ed. F. D. King, The Royal Society of Chemistry, Cambridge, UK, 1994, which is incorporated herein by reference in its entirety.

It should further be understood that solvates (e.g., hydrates) of the compounds of formula I are also with the scope of the invention. Methods of solvation are generally known in the art.

"Stable compound" and "stable structure" are meant to indicate a compound that is sufficiently robust to survive isolation to a useful degree of purity from a reaction mixture, and formulation into an efficacious therapeutic agent. It is preferred that these recited compounds do not contain a N-halo, $S(O)_2H$, or $S(O)H$ group.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the invention that is effective when administered alone or in combination. "Therapeutically effective amount" is also intended to include an amount of the combination of compounds claimed that is effective to inhibit Trk related diseases and/or conditions. The combination of compounds is preferably a synergistic combination. Synergy, as described, for example, by Chou and Talalay, *Adv. Enzyme Regul.* 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

The invention further includes compositions comprising one or more compounds of the invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., Mack Publishing Company, Easton, Pa., 1985, which is incorporated herein by reference in its entirety.

Utility

According to a further aspect of the invention, there is provided the use of a compound of the formula I, or a pharmaceutically acceptable salt thereof in the manufacture of a medicament for use in the production of an antiproliferative effect in a warm-blooded animal such as a human being.

According to a further feature of the invention there is provided a method for producing an antiproliferative effect in a warm-blooded animal, such as a human being, in need of such treatment which comprises administering to said animal an effective amount of a compound of formula I or a pharmaceutically acceptable salt thereof as defined herein before.

Further, another aspect of the invention provides for the use of a compound of formula I or a pharmaceutically acceptable salt thereof in the manufacture of a medicament for use in the treatment of certain types of cancer including cancer of the prostate, pancreatic ductal adreno-carcinoma, breast, colon, lung, ovary, pancreas, thyroid, neuroblastoma, glioblastoma, medulloblastoma, melanoma, multiple myeloma or acute myelogenous leukemia (AML).

The anti-proliferative treatment defined herein before may be applied as a sole therapy or may involve, in addition to a compound of the invention, one or more other substances and/or treatments. Such treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

The term "anti-cancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (Avastin®) and small molecules such as ZD6474 and SU6668; Vatalanib, BAY-43-9006, SU11248, CP-547632, and CEP-7055; HER 1 and HER 2 inhibitors including anti-HER2 antibodies (Herceptin); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, e.g. Gleevec® and dasatinib (Sprycel®), Casodex® (bicalutamide, Astra Zeneca), Tamoxifen; MEK-1 kinase inhibitors, MAPK kinase inhibitors, PI3 kinase inhibitors; PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (ixabepilone), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g. 6-thioguanine and 6-mercaptopurine; glutamine antagonists, e.g. DON (AT-125; d-oxo-norleucine); ribonucleotide reductase inhibitors; mTOR inhibitors; and haematopoietic growth factors.

Additional cytotoxic agents include cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

In the field of medical oncology it is normal practice to use a combination of different forms of treatment to treat each patient with cancer. In medical oncology the other component(s) of such treatment in addition to the antiproliferative treatment defined herein before may be surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example, megestrol acetate), aromatase inhibitors (for example, anastrozole, letrozole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors such as marimastat and inhibitors of urokinase plasminogen activator receptor function) and inhibitors of growth factor function, (such growth factors include for example, EGF, FGF, platelet derived growth factor and hepatocyte growth factor, such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates such as methotrexate, fluoropyrimidines such as 5-fluorouracil, purine and adenosine analogues, cytosine arabinoside); Intercalating antitumour antibiotics (for example, anthracyclines such as doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine, vinorelbine, vinblastine and vinflunine) and taxoids such as Taxol® (paclitaxel), Taxotere® (docetaxel) and newer microbtubule agents such as epothilone analogs (ixabepilone), discodermolide analogs, and eleutherobin analogs; topoisomerase inhibitors (for example, epipodophyllotoxins such as etoposide and teniposide, amsacrine, topotecan, irinotecan); cell cycle inhibitors (for example, flavopyridols); biological response modifiers and proteasome inhibitors such as Velcade® (bortezomib).

As stated above, the formula I compounds of the invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the prostate, pancreatic ductal adreno-carcinoma, breast, colon, lung, ovary, pancreas, and thyroid;

tumors of the central and peripheral nervous system, including neuroblastoma, glioblastoma, and medulloblastoma;

hematological malignancies such as acute myelogenous leukemia (AML), and other tumors, including melanoma and multiple myeloma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease.

The compounds of formula I are especially useful in treatment of tumors having a high incidence of tyrosine kinase activity, such as prostate, colon, brain, thyroid and pancreatic tumors. Additionally, the compounds of the invention may be useful in treatment of sarcomas and pediatric sarcomas. By the administration of a composition (or a combination) of the compounds of this invention, development of tumors in a mammalian host is reduced.

Compounds of formula I may also be useful in the treatment of other cancerous diseases (such as acute myelogenous leukemia) that may be associated with signal transduction pathways operating through kinases such as Flt-3 (Fme-like kinase-3), Tie-2, CDK2, VEGFR, FGFR and IGFR kinases.

The pharmaceutical compositions of the invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The pharmaceutical compositions may be in the form of sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulsion.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS.™. Model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

The compounds may be administered in a dosage range of about 0.05 to 200 mg/kg/day, preferably less than 100 mg/kg/day, in a single dose or in 2 to 4 divided doses.

Biological Assays

A IGF1-Receptor Tyrosine Kinase Assay

The assays were performed in U-bottom 384-well plates. The final assay volume was 30 μl prepared from 15 μl additions of enzyme and substrates (fluoresceinated IGF1R substrate peptide and ATP) and test compounds in assay buffer (100 mM HEPES pH 7.4, 10 mM $MnCl_2$, 0.015% Brij35 and 4 mM DTT). The reaction was initiated by the combination of IGF1-receptor with substrates and test compounds. The reaction was incubated at room temperature for 60 min. and terminated by adding 30 μl of 35 mM EDTA to each sample. The reaction mixture was analyzed on the Caliper LabChip 3000 by electrophoretic separation of the fluorescent substrate and phosphorylated product Inhibition data were calculated by comparison to no enzyme control reactions for 100% inhibition and vehicle-only reactions for 0% inhibition. The final concentration of reagents in the assays are ATP, 25 μM; FL-peptide, 1.5 μM; IGF1-Receptor, 14 nM; and DMSO, 1.6%. Dose response curves were generated to determine the concentration required inhibiting 50% of kinase activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

Compounds described herein were tested in the above assay. The following results were obtained.

TABLE 1

| IGF-1R in vitro kinase IC50 (uM) | |
|---|---|
| Example | IGF1R kinase $IC_{50}$ (uM) |
| 2 | 0.020 |
| 3 | 0.002 |
| 4 | 0.062 |

Methods of Preparation

In general, the compounds of Formula (I) can be prepared in accordance with the following Schemes and the general knowledge of one skilled in the art. Tautomers and solvates (e.g., hydrates) of the compounds of Formula (I) are also within the scope of invention. Methods of solvation are generally known in the art. Accordingly, the compounds of the instance invention can be in the free or hydrate form, and can be obtained by methods exemplified in the following Schemes.

Scheme 1

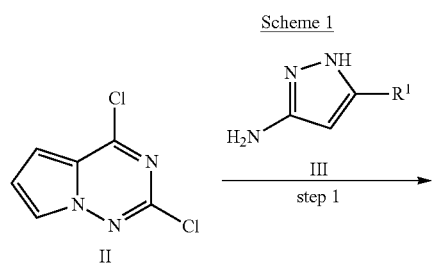

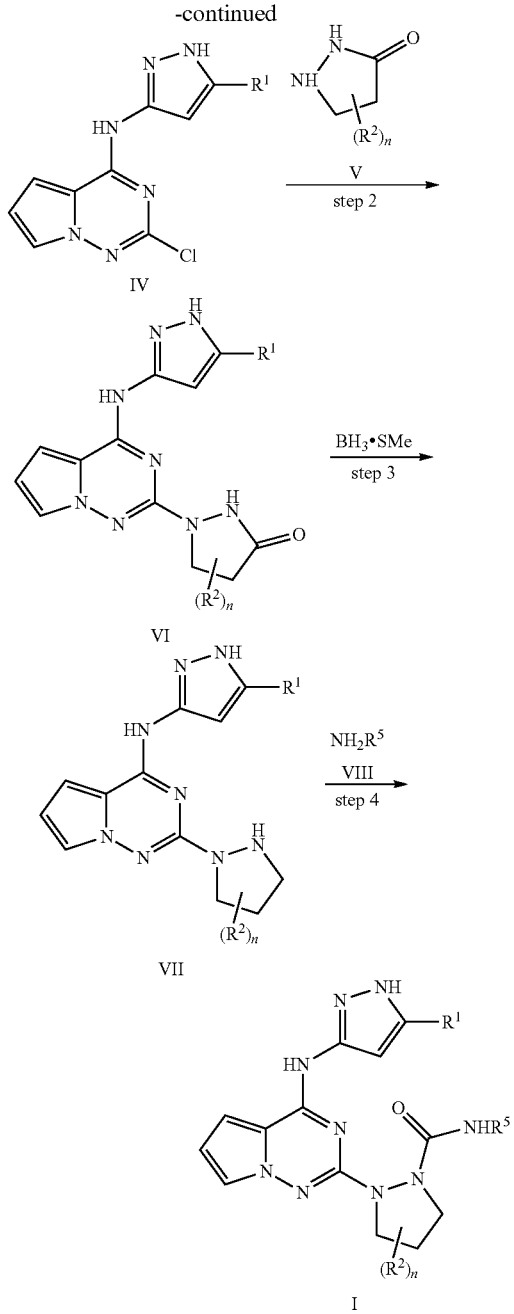

Step 1
Compound IV is produced by treating compound II with an appropriately substituted 2-amino pyrazole (III) in the presence of a base, such as for example, diisopropylethylamine in a solvent, such as isopropanol.

Step 2
Compound VI is obtained by treating compound IV with an appropriately functionalized pyrazolidin-3-one in the presence of a base, such as, for example, diisopropylethylamine, in an organic solvent such as NMP or DMF while heating. Alternatively, transition metal catalyzed methods for introduction of amino compound V may also be used.

Step 3
Compound VII can be obtained by treating VI with reducing agents such as, for example, borane dimethyl sulfide complex in an organic solvent such as THF.

Step 4

Compound I can be obtained by treating VII with appropriately substituted phenyl carbamates in the presence of a base such as, for example diisopropylethylamine Alternatively, these ureas can be made in accordance with the general knowledge of one skilled in the art.

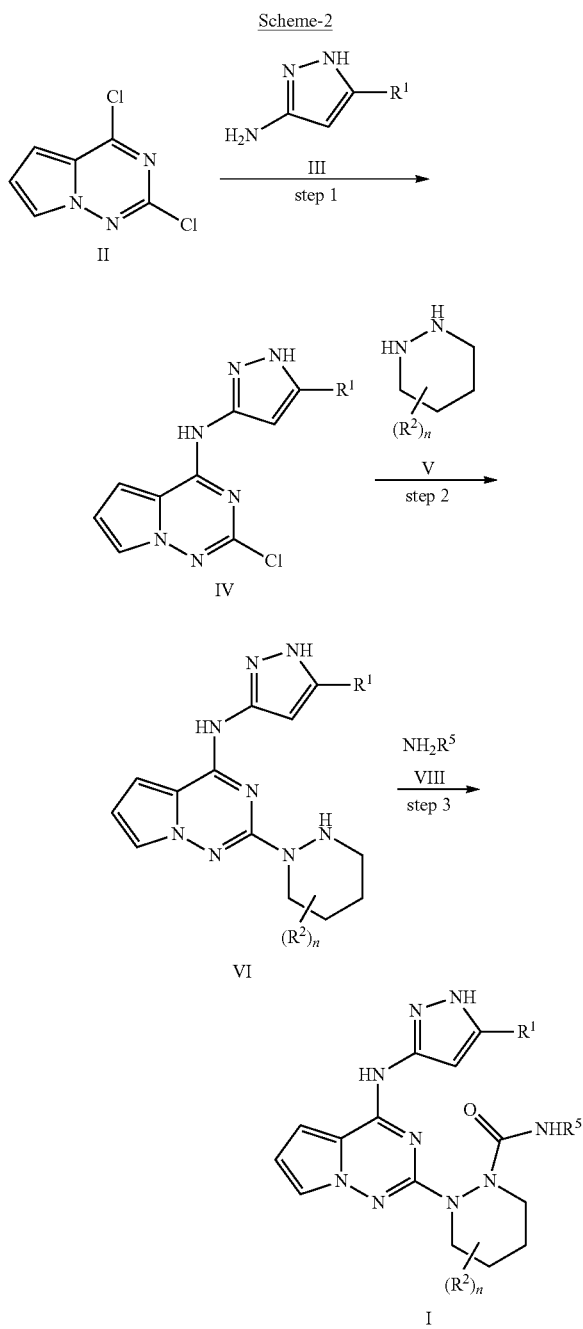

Step 1

Compound IV is produced by treating compound II with an appropriately substituted 2-Amino pyrazole (III) in the presence of a base, such as for example, diisopropylethylamine in a solvent, such as isopropanol.

Step 2

Compound VI is obtained by treating compound IV with an appropriately functionalized hexahydropyradiazine in the presence of a base, such as, for example, diisopropylethylamine in an organic solvent such as NMP or DMF while heating. Alternatively, transition metal catalyzed methods for introduction of amino compound V may also be used.

Step 3

Compound I can be obtained by treating VI with appropriately substituted phenyl carbamates in the presence of a base such as, for example diisopropylethylamine. Alternatively, these ureas can be made in accordance with the general knowledge of one skilled in the art.

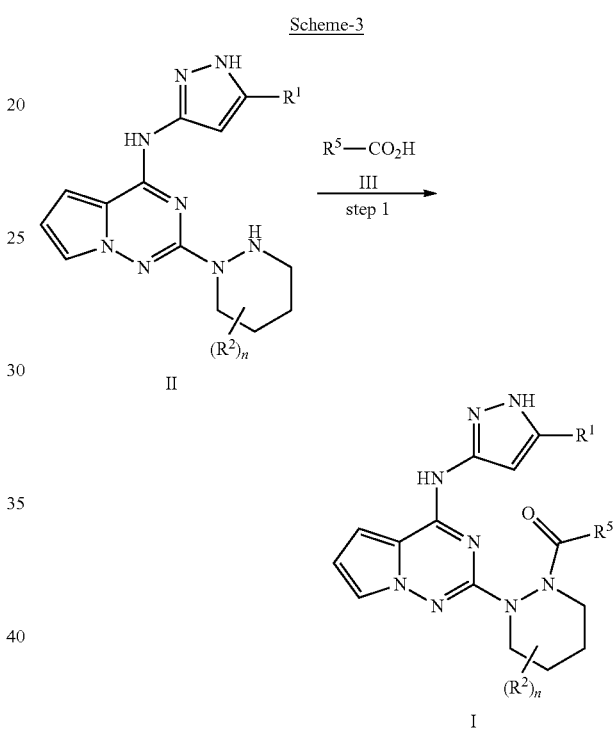

Step 3

Compound I can be obtained by coupling II with the appropriately substituted aryl or heteroaryl carboxylic acid III using reagents that form amide bonds such as, for example, (benzotriazol-1-yolxy)tripyrrollidinophosphonium hexafluorophosphate and a base, such as, for example, diisopropylethylamine in a solvent such as, for example, dimethylformamide.

EXAMPLES

The invention is further defined in the following Examples. It should be understood that these Examples are given by way of illustration only. From the above discussion and this Example, one skilled in the art can ascertain the essential characteristics of this invention, and without departing from the spirit and scope thereof, can make various changes and modifications to the invention to adapt the invention to various uses and conditions. As a result, the invention is not limited by the illustrative examples set forth hereinbelow, but rather defined by the claims appended hereto.

Example 1

2-(4-(3-Cyclopropyl-1H-pyrazol-5-ylamino)pyrrolo[1,2-f][1,2,4]triazin-2-yl)-N-(6-fluoropyridin-3-yl)pyrazolidine-1-carboxamide

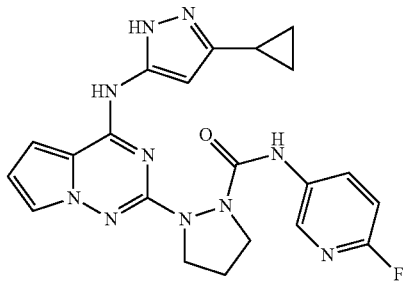

1A. 2-Chloro-N-(3-cyclopropyl-1H-pyrazol-5-yl)pyrrolo[1,2-f][1,2,4]triazin-4-amine

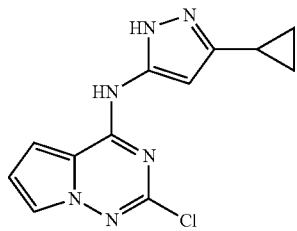

A mixture of 2,4-dichloropyrrolo[1,2-f][1,2,4]triazine (977 mg, 5.2 mmole), 5-cyclopropyl-1H-pyrazol-3-amine (640 mg, 1 equiv), and diisopropylethylamine (1.54 mL, 1.7 equiv) in isopropyl alcohol (5 mL) was stirred at room temperature overnight. The product was collected by filtration (1.18 gm, 83% yield): MS: 275 (M+H)$^+$; HPLC Ret Time: 1.56 min. (Phenomenex-Luna s10 3.0×50 mm column, 3 min gradient, 4 mL/min).

1B. (1-(4-(3-Cyclopropyl-1H-pyrazol-5-ylamino)pyrrolo[1,2-f][1,2,4]triazin-2-yl))pyrazolidin-3-one

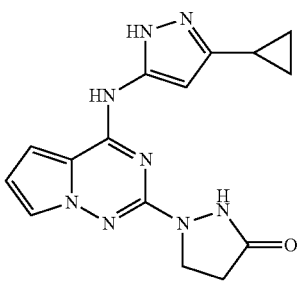

To a stirred solution of 1 gm (3.63 mmol) of 2-chloro-N-(3-cyclopropyl-1H-pyrazol-5-yl)pyrrolo[1,2-f][1,2,4]triazin-4-amine 1A in 10 mL of NMP was added 5 mL of Hunig's base, followed by 1.33 gm (10.91 mmol) of the HCl salt of pyrazolidin-3-one. The mixture was heated at 145° C. for 24 h, cooled, diluted with water and extracted with ethyl acetate. The combined organic layer was washed with water, brine and dried (Na$_2$SO$_4$). Evaporation of the solvent furnished a crude residue which was subjected to preparative HPLC to give 1B. $^1$H NMR (CH$_3$OD, 500 MHz) δ7.59 (s, 1H), 7.04 (d, 1H, J=4.27 Hz), 6.66 (s, 1H, m), 6.26 (s, 1H) 4.22 (t, 2H, J=8.39 Hz) 2.59-2.76 (m, 2H), 1.93-2.08 (m, 1H) 1.01-1.17 (m, 2H), 0.74-0.92 (m, 2H) MS: 325 (M+H)$^-$, HPLC Ret time: 3.24 min (Phenomenex-Luna s10 3.0×50 mm column, 3 min gradient, 4 mL/min)

1C. N-(3-Cyclopropyl-1H-pyrazol-5-yl)-2-(pyrazolidin-1-yl)pyrrolo[1,2-f][1,2,4]triazin-4-amine

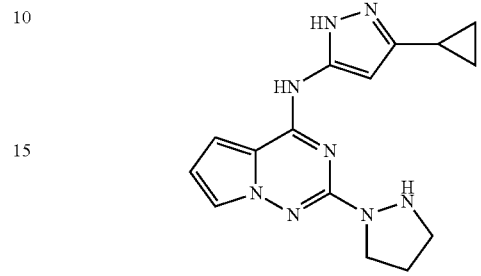

To a stirred solution of 250 mg (0.769 mmol) of the (1-(4-(3-cyclopropyl-1H-pyrazol-5-ylamino)pyrrolo[1,2-f][1,2,4]triazin-2-yl)pyrazolidin-3-one 1B in 5mL of THF was added 0.22 mL (2.31 mmol) of borane dimethylsulfide complex. The mixture was stirred for 24 h, quenched with methanol and refluxed for 14 h. The mixture was cooled and the solvent was evaporated to dryness and residue was subjected to preparative HPLC to furnish 1C. MS: 311 (M+H)$^+$, HPLC Ret time: 2.00 min (Phenomenex-Luna s10 3.0×50 mm column, 3 min gradient, 4 mL/min)

To a stirred solution of N-(3-cyclopropyl-1H-pyrazol-5-yl)-2-(pyrazolidin-1-yl)pyrrolo[1,2-f][1,2,4]triazin-4-amine 1C (40 mg, 0.129 mmol) in DMSO (3 mL) was added 1 mL of Hunig's base, followed by 6 mg (0.258 mmol of phenyl 6-fluoropyridin-3-ylcarbamate. The mixture was stirred for 2 h, and the reaction mixture was subjected to preparative HPLC. The HPLC fractions containing the product were passed through the MCX cartridge, washed with methanol and the product was released with 2N solution of ammonia in methanol. Removal of the solvents furnished the product 1. MS: 449 (M+H)$^+$, HPLC Ret time: 1.67 min (Phenomenex-Luna s10 4.6×50 mm column, 4 min gradient, 4 mL/min).

Example 2

2-(4-(3-cyclopropyl-1H-pyrazol-5-ylamino)pyrrolo[1,2-f][1,2,4]triazin-2-yl)-N-(6-fluoropyridin-3-yl)piperazine-1-carboxamide

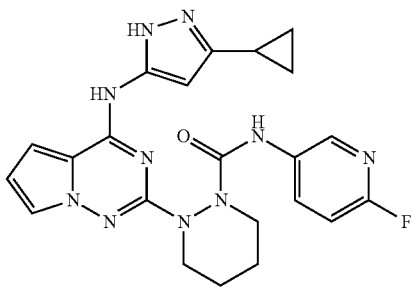

2A N-(3-Cyclopropyl-1H-pyrazol-5-yl)-2-(piperazin-1-yl)pyrrolo[1,2-f][1,2,4]triazin-4-amine

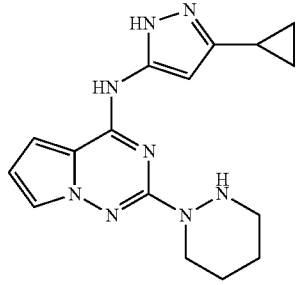

A 2-chloro-N-(3-cyclopropyl-1H-pyrazol-5-yl)pyrrolo[1,2-f][1,2,4]triazin-4-amine 1A (890 mg, 0.325 mmol), and 1 gm (0.813 mmol) of HCl salt of hexahydropyradiazine were taken in 7 mL of NMP to which was added 3 mL of Hunig's base. The mixture was heated at 140° C. for 24 h, cooled, and the mixture was subjected to preparative HPLC to afford the product 2A. MS: 325 (M+H)$^+$, HPLC Ret time: 1.52 min (Phenomenex-Luna s10 4.6×50 mm column, 2 min gradient, 4 mL/min)

To a stirred solution of 60 mg (0.185 mmol) of the 2A in 2 mL of DMSO and 1 mL of Hunig's base was added 47 mg (8.20 mml) of phenyl 6-fluoropyridin-3-ylcarbamate. The mixture was stirred for 3 h and then subjected to preparative HPLC. The HPLC fractions containing the product were passed through the MCX cartridge, washed with methanol and the product was released with 2N solution of ammonia in methanol. Removal of the solvents furnished the product 2. MS: 463 (M+H)$^+$, HPLC Ret time: 1.75 min (Phenomenex-Luna s10 4.6×50 mm column, 2 min gradient, 4 mL/min)

Example 3

2-(4-(3-Cyclopropyl-1H-pyrazol-5-ylamino)pyrrolo[1,2-f][1,2,4]triazin-2-yl)-N-(thiazol-2-yl)piperazine-1-carboxamide

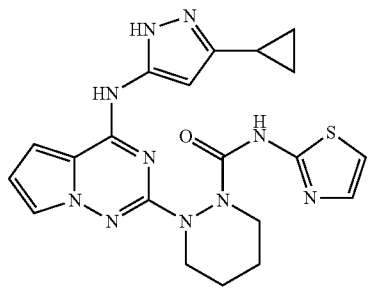

To a stirred solution of 50 mg (0.15 mmol) of 2A in 2 mL of DMSO and 1 mL of Hunig's base was added 51 mg (0.23 mmol) of phenyl thiazol-2-ylcarbamate. The mixture was heated at 50° C. for 2 h, cooled, and subjected to preparative HPLC. The HPLC fractions containing the product were passed through the MCX cartridge, washed with methanol and the product was released with 2N solution of ammonia in methanol. Removal of the solvents furnished the product 3. MS: 451 (M+H)$^+$, HPLC Ret time: 1.75 min (Phenomenex-Luna s10 4.6×50 mm column, 2 min gradient, 4 mL/min)

Example 4

(2-(4-(3-cyclopropyl-1H-pyrazol-5-ylamino)pyrrolo[1,2-f][1,2,4]triazin-2-yl)piperazin-1-yl)(thiazol-2-yl)methanone

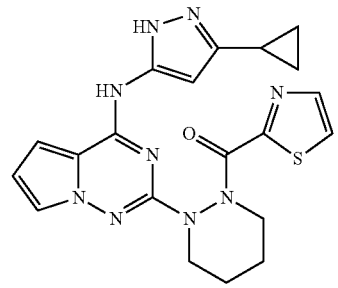

To a stirred solution of 65 mg (0.2 mmol) of 2A in a mixture of 1 mL of NMP and 1 mL of methanol was added 0.5 mL of thiazole-2-carbonyl chloride. The mixture was stirred for 1 h, and subjected to preparative HPLC. The HPLC fractions containing the product were passed through the MCX cartridge, washed with methanol and the product was released with 2N solution of ammonia in methanol. Removal of the solvents furnished the product 4. MS: 436 (M+H)$^+$, HPLC Ret time: 1.8 min (Phenomenex-Luna s10 4.6×50 mm column, 2 min gradient, 4 mL/min).

Example 5

(2-(4-(3-Cyclopropyl-1H-pyrazol-5-ylamino)pyrrolo[1,2-f][1,2,4]triazin-2-yl)piperazin-1-yl)(6-fluoropyridin-3-yl)methanone

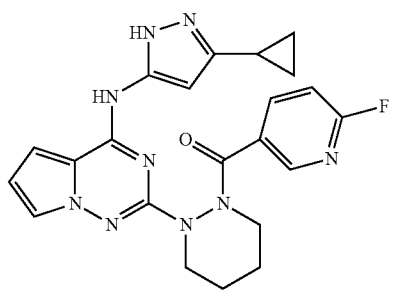

To a stirred solution of 37 mg (0.2 mmol) of 6-fluoronicotinic acid in 2 mL of NMP and 1 mL of Hunig's base was added 99 mg (0.26 mmol) of HATU. The mixture was stirred for 10 min and a solution of 65 mg (0.20 mmol) of 2A in 2 mL of NMP was added. The mixture was stirred for 6 h and subjected to preparative HPLC. The HPLC fractions containing the product were passed through the MCX cartridge, washed with methanol and the product was released with 2N solution of ammonia in methanol. Removal of the solvents furnished the product 5. MS: 448 (M+H)+, HPLC Ret time: 1.88 min (Phenomenex-Luna s10 4.6×50 mm column, 2 min gradient, 4 mL/min).

Example 6

(2-(4-(3-Cyclopropyl-1H-pyrazol-5-ylamino)pyrrolo[1,2-f][1,2,4]triazin-2-yl)piperazin-1-yl)(pyrazin-2-yl)methanone

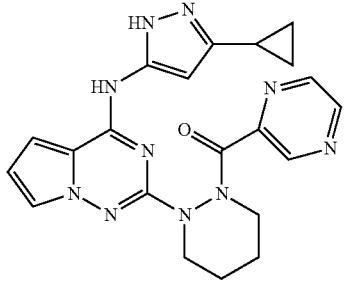

To a stirred solution of 30 mg (0.09 mmol) of 2A in 2 mL of NMP and 1 mL of Hunig's base was added 17.3 mg (0.26 mmol) of pyrazine-2-carboxylic acid, followed by 53 mg (0.13 mmol) HATU. The mixture was stirred for 3 h, and then subjected to preparative HPLC. The HPLC fractions containing the product were passed through the MCX cartridge, washed with methanol and the product was released with 2N solution of ammonia in methanol. Removal of the solvents furnished the product 4. MS: 431 (M+H)+, HPLC Ret time: 1.74 min (Phenomenex-Luna s10 4.6×50 mm column, 2 min gradient, 4 mL/min).

We claim:

1. A compound of formula I

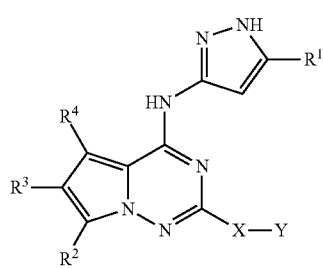

wherein:
X is a heterocyclyl group containing 2 or more heteroatoms;
Y is $COR^5$ or $CONHR^5$;
$R^1$ is hydrogen, alkyl, substituted alkyl, amide, substituted amide, cycloalkyl or substituted cycloalkyl;
$R^2$, $R^3$ and $R^4$ are independently hydrogen, alkyl, substituted alkyl, hydroxy, alkoxy, substituted alkoxy, halogen, amino, substituted amino, aminoalkyl, substituted aminoalkyl, alkylamino, substituted alkylamino, amide, substituted amide, carbamate, ureido or —CN;
$R^5$ is heteroaryl or substituted heteroaryl;
or a pharmaceutically acceptable salt, tautomer or stereoisomer thereof.

2. A compound of formula I

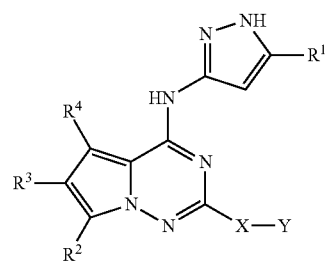

wherein
X is pyrazolidine or piperazine;
$R^1$ is cycloalkyl or substituted cycloalkyl;
$R^5$ is thiazole, pyrazine or substituted pyrazine, pyridine or substituted pyridine,
or a pharmaceutically acceptable salt or stereoisomer thereof.

3. The compound according to claim 2 wherein $R^2$, $R^3$ and $R^4$ are independently hydrogen or $C_1$-$C_4$ alkyl.

4. A compound selected from the group consisting of
2-(4-(3-Cyclopropyl-1H-pyrazol-5-ylamino)pyrrolo[1,2-f][1,2,4]triazin-2-yl)-N-(6-fluoropyridin-3-yl)pyrazolidine-1-carboxamide,
2-(4-(3-cyclopropyl-1H-pyrazol-5-ylamino)pyrrolo[1,2-f][1,2,4]triazin-2-yl)-N-(6-fluoropyridin-3-yl)piperazine-1-carboxamide,
2-(4-(3-Cyclopropyl-1H-pyrazol-5-ylamino)pyrrolo[1,2-f][1,2,4]triazin-2-yl)-N-(thiazol-2-yl)piperazine-1-carboxamide,
(2-(4-(3-cyclopropyl-1H-pyrazol-5-ylamino)pyrrolo[1,2-f][1,2,4]triazin-2-yl)piperazin-1-yl)(thiazol-2-yl)methanone,
(2-(4-(3-Cyclopropyl-1H-pyrazol-5-ylamino)pyrrolo[1,2-f][1,2,4]triazin-2-yl)piperazin-1-yl)(6-fluoropyridin-3-yl)methanone, and
(2-(4-(3-Cyclopropyl-1H-pyrazol-5-ylamino)pyrrolo[1,2-f][1,2,4]triazin-2-yl)piperazin-1-yl)(pyrazin-2-yl)methanone
or a pharmaceutically acceptable salt or stereoisomer thereof.

5. A pharmaceutical composition comprising a pharmaceutically acceptable carrier and one or more compounds of claim 1 or pharmaceutically acceptable salts or stereoisomers thereof.

6. A pharmaceutical composition comprising a pharmaceutically acceptable carrier and one or more compounds of claim 1 or pharmaceutically acceptable salts or stereoisomers thereof in combination with one or more other anti-cancer or cytotoxic agents.

7. A pharmaceutical composition comprising a pharmaceutically acceptable carrier and one or more compounds of claim 2 or pharmaceutically acceptable salts or stereoisomers thereof.

8. A pharmaceutical composition comprising a pharmaceutically acceptable carrier and one or more compounds of claim 3 or pharmaceutically acceptable salts or stereoisomers thereof.

9. A pharmaceutical composition comprising a pharmaceutically acceptable carrier and one or more compounds of claim 4 or pharmaceutically acceptable salts or stereoisomers thereof.

* * * * *